United States Patent [19]

Romano et al.

[11] Patent Number: 4,670,606
[45] Date of Patent: Jun. 2, 1987

[54] PROCESS FOR SEPARATING LINEAR-CHAIN OXO-ALCOHOLS FROM MIXTURES OF LINEAR AND BRANCHED-CHAIN OXO-ALCOHOLS

[75] Inventors: Ugo Romano, Vimercate; Giacomo Sasselli, S.Donato Milanese; Luigi Raisa, Induno Olona, all of Italy

[73] Assignee: Chimica Augusta, S.p.A., Palermo, Italy

[21] Appl. No.: 699,999

[22] Filed: Feb. 8, 1985

[30] Foreign Application Priority Data

Feb. 24, 1984 [IT] Italy .................................. 19788 A/84

[51] Int. Cl.[4] ............................................. C07C 45/81
[52] U.S. Cl. ................................................... 568/410
[58] Field of Search ....................... 568/410, 492, 923; 260/428.5

[56] References Cited

U.S. PATENT DOCUMENTS 3,093,649  6/1963  Ratji et al. ........................... 568/410

FOREIGN PATENT DOCUMENTS 53-71003   6/1978   Japan ................................... 568/410
 698217  10/1953   United Kingdom ................ 568/923
 964649   7/1964   United Kingdom ................ 568/923
1001653  12/1965   United Kingdom ................ 568/923
1419299  12/1975   United Kingdom ................ 568/873

OTHER PUBLICATIONS

Chem. Abst., vol. 94, #102852n (1981).

Primary Examiner—James H. Reamer
Attorney, Agent, or Firm—Morgan & Finnegan

[57] ABSTRACT

A mixture of linear and branched-chain detergent oxo-alcohols, containing from 11 to 16 carbon atoms in the molecule, is dissolved in a hydrocarbon or ether solvent, and the solution thus obtained is cooled to obtain a dispersion of a solid phase in a liquid phase.

The solid phase constituting the linear-chain oxo-alcohol fraction is separated and recovered. The branched-chain oxo-alcohol fraction is separated and recovered from the liquid phase.

6 Claims, No Drawings

PROCESS FOR SEPARATING LINEAR-CHAIN OXO-ALCOHOLS FROM MIXTURES OF LINEAR AND BRANCHED-CHAIN OXO-ALCOHOLS

This invention relates to a process for separating essentially linear-chain oxo-alcohols from a mixture of linear-chain and branched-chain detergent oxo-alcohols.

Oxo-alcohols are known products, which are obtained industrially by the hydroformylation of olefins by means of carbon monoxide and hydrogen, over a cobalt or rhodium catalyst. Oxo-alcohols containing from 11 to 16 carbon atoms in the molecule, and obtained by the hydroformylation of linear or essentially linear olefins with a terminal or internal double bond, are also known as detergent oxo-alcohols and find their main application in the detergent field and in components for lubricating oils. Such detergent oxo-alcohols are always a mixture of linear and branched-chain oxo-alcohols in a ratio which depends mainly on the particular hydroformylation catalyst used. With regard to the production technology, characteristics and uses of oxo-alcohols, reference should be made to the following literature:

Kirk Othmer, "Encyclopedia of Chemical Technology" 3rd Ed. vol 16, pages 637–653; "Monohydric Alcohols: Manufacture, Applications and Chemistry", E. J. Wickson, Ed. Am. Chem. Soc. 1981.

The present invention relates in particular to the detergent oxo-alcohol sector, this term signifying those oxo-alcohols which contain from 11 to 16 carbon atoms in their molecule and which are obtained by the hydroformylation, using carbon monoxide and hydrogen, of linear or essentially linear olefins with a terminal or internal double bond, and containing a linear fraction of between about 40% and about 80%, according to the particular catalyst used in the hydroformylation. In the detergent field, linear detergent oxo-alcohols or those in which the linear fraction is as high as possible are desirable for biodegradation reasons.

On the other hand, branched-chain oxo-alcohols or those in which the branched-chain fraction is as high as possible are desirable in the lubricating oil additives field because of the capacity of such a fraction to depress the freezing point of the lubricating oil. The detergent oxo-alcohols obtained by current commercial processes do not completely satisfy these requirements, as their linear fraction content varies from about 40% to about 80%.

It has now been found possible, according to the present invention, to separate linear-chain oxo-alcohols from commercial detergent oxo-alcohol mixtures by a simple and convenient process, which enables the aforesaid problems to be solved.

More particularly, according to the present invention:

a mixture of linear and branched-chain detergent oxo-alcohols containing from 11 to 16 carbon atoms in the molecule is dissolved in a liquid hydrocarbon solvent containing from 3 to 5 carbon atoms in the molecule, or in methyl tert-butylether;

the resultant solution is cooled to a temperature in the range of $-20°$ to $-52°$ C., until a solid phase separates, dispersed in a liquid phase;

the solid phase, constituted by the linear-chain oxo-alcohol fraction, is separated and recovered; and the branched-chain oxo-alcohol fraction is separated and recovered from the liquid phase.

All those mixtures of detergent oxo-alcohols containing one or more homologue oxo-alcohols chosen from those containing from 11 to 16 carbon atoms in the molecule and having a linear fraction content which varies from about 40% to about 80% can be subjected to the process of the present invention.

The detergent oxo-alcohol mixtures which are generally subjected to the process of the present invention are those containing from 2 to 4 homologues chosen from those having from 12 to 15 carbon atoms in the molecule, and of which the linear content varies within the aforesaid range.

The solvents suitable for crystallisation of the linear oxo-alcohols are those hydrocarbons containing from 3 to 5 carbon atoms in the molecule, such as propane, n-butane, isobutane, n-pentane and iso-pentane. A further solvent suitable for this purpose is methyl tert-butylether.

According to the process of the present invention, a solution of the detergent oxo-alcohols in the prechosen solvent is formed with a volumetric constituent ratio of between 25:75 and 50:50. In this respect, it is not convenient to use a ratio of less than 25:75 for process economy reasons.

On the other hand a ratio exceeding 50/50 is undesirable in that it gives rise to systems which are difficult to treat from a rheological viewpoint.

According to the present invention, the solution of detergent oxo-alcohols in the chosen solvent is cooled to a temperature in the range of $-20°$ to $-52°$ C., the chosen temperature being within the lower part of the range in the case of mixtures of lower molecular weight oxo-alcohols.

Under these conditions, a crystalline precipitate forms constituted exclusively or essentially of the linear-chain oxo-alcohols. In practice, the cooled mass is kept under slight agitation for a time at least sufficient to reach equilibrium conditions, or at least conditions close to equilibrium conditions, for the chosen crystallisation temperature. Such times vary generally from 10 to 30 minutes. The dispersion obtained in this manner is then treated to separate the solid phase from the liquid phase. This separation, which is conducted within a temperature range of $-20°$ to $-52°$ C., and preferably at a temperature equal or close to that to which the initial solution was cooled, can be conducted by conventional means such as filtration or centrifuging, and the separated precipitate can be washed with a cold solvent, for example, a solvent of the same kind as that used for the precipitation.

In all cases, a solid phase separates constituted exclusively or essentially of linear-chain oxo-alcohols.

In this respect, the linear oxo-alcohol concentration in this solid phase exceeds 90%, and, in general, is greater than 95% and up to 100%. This solid phase is liquefied and recovered. In this treatment, a liquid phase also separates, this phase constituting the solvent in which the fraction rich in branched-chain oxo-alcohols is dissolved. These latter are recovered by evaporating the solvent. In all cases, the linear and branched-chain fractions separated in this manner have the same mean molecular weight as the initial detergent oxo-alcohol mixture subjected to treatment.

The process of the present invention is simple and economical, and enables linear oxo-alcohols to be separated from their mixtures with branched-chain oxo-alcohols, with yields of up to about 97%. Whatever the complexity of the mixtures subjected to treatment, it is possible to obtain linear oxo-alcohols in pure or substantially pure form. The process of the present invention requires simple, readily available apparatus. Thus, the precipitation can be carried out in vessels such as an autoclave, fitted with an agitator and cooling means. Alternatively, according to a further embodiment in which propane is used as the solvent, the cooling is effected by evaporating a fraction of the solvent directly from the crystallisation vessel.

In this case, typically, liquid propane and the detergent oxo-alcohol mixture are fed to the crystallisation vessel in a volumetric ratio of 60:40.

The use of propane as the solvent enables crystallisation to be conducted at about −36° C., operating at a pressure slightly greater than atmospheric. The solid phase can be separated from the solution by a centrifuge-decanter connected to the crystallizer. The solid thus separated is liquefied in a circulation evaporator, from which the impregnating propane escapes. The separated liquid can be used for precooling the propane fed to the crystallisation vessel, and can then be fed to a train of two evaporators in series in order to separate the propane from the branched-chain oxo-alcohol fraction.

Conveniently, the first evaporator operates at a pressure of about 15 atmospheres which enables the propane to be fed directly to the condenser. The second evaporator conveniently operates at atmospheric pressure so as to completely remove the propane. The propane fraction evaported in the crystallisation vessel and that originating from the second evaporator are drawn by a compressor and compressed to a pressure of 13.5 atmospheres, at which pressure the propane condenses at about 37° C., using cooling-tower water. The condenser also receives the propane fraction originating from the first evaporator (about 40% of the total). The liquid propane is further cooled to about 0° C. by heat exchange with the liquid stream separated in the centrifuge, and is then fed to the crystallisation vessel together with the detergent oxo-alcohol feed.

In the experimental examples given hereinafter for non-limiting illustrative purposes, detergent oxo-alcohols are treated which have been obtained by the hydroformylation of substantially linear olefins, having an internal or terminal double bond, using hydrogen and carbon monoxide over a cobalt catalyst.

More particularly, the following detergent oxo-alcohol mixtures are treated:

OA-125: a liquid mixture of detergent oxo-alcohols containing from 12 to 15 carbon atoms in the molecule, of mean molecular weight 205.5, and with 55.6% by weight of branched-chain fraction and 44.4% by weight of linear fraction.

OA-123: a liquid mixture of detergent oxo-alcohols containing 12 and 13 carbon atoms in the molecule, of mean molecular weight 193.75, and with 51.1% by weight of branched-chain fraction and 42.9% by weight of linear fraction.

OA-145: a liquid mixture of oxo-alcohols containing 14 and 15 carbon atoms in the molecule, of mean molecular weight 221.65, and with 59.1% by weight of branched-chain fraction and 40.9% by weight of linear fraction.

The aforesaid characteristics of the detergent oxo-alcohol mixtures were determined by gas chromatography analysis.

EXAMPLES 1-11

The tests of these examples are conducted in an apparatus consisting of a 500 ml jacketed flask fitted with a bladed mechanical agitator, thermometer, and bottom outlet. This latter is connected to a filtration device provided with a G3 porous baffle, and temperature-controlled with the aid of a central refrigeration unit.

350 ml of a solution of oxo-alcohols chosen from the described mixtures dissolved in the chosen solvent are fed into the flask and the flask contents are agitated and cooled to the predetermined temperature. After the temperature has stabilised at the chosen value, the flask contents are kept under agitation for approximately a further 20 minutes, to enable the solid/liquid system to reach equilibrium, or a situation close to equilibrium, under the operating conditions. The flask contents are then transferred to the filtration device, which is temperature-controlled at the same temperature as the flask, in order to separate the solid phase from the liquid phase.

The solid phase is melted by allowing the temperature to rise to ambient temperature, and is then subjected to gas chromatography analysis. The analysis shows that in all cases the product consists of linear oxo-alcohols (purity up to 99%) with a mean molecular weight practically unchanged from that of the initial mixture.

The solvent is separated from the liquid phase (filtrate) by evaporation, and the residue is subjected to gas chromatography analysis to determine the composition of the oxo-alcohols present in the liquid phase (filtrate) and their mean molecular weight.

The results are shown in Tables 1 to 4 below, which also show:

the oxo-alcohol mixtures subjected to treatment,
the volumetric ratio of oxo-alcohol mixture to chosen solvent,
the chosen solvent,
the temperature to which the solution is cooled and the filtration temperature.

TABLE 1

Oxo-alcohols: OA-125
Volumetric ratio oxo-alcohols/solvent = 25:75

| Ex. No. | Solvent | temperature to which cooled and filtered (°C.) | branched-chain components in liquid phase (% by weight) | mean molecular weight of oxo-alcohols in liquid phase |
|---|---|---|---|---|
| 1 | butane | −21.2 | 72.5 | 205.1 |
| 2 | iso-pentane | −25.4 | 79.7 | 205.0 |
| 3 | n-pentane | −31.2 | 85.0 | 204.3 |
| 4 | methyl tert-butyl ether | −35.4 | 83.5 | 205.1 |

TABLE 2

Solvent: n-pentane
Volumetric ratio oxo-alcohols/solvent = 25:75

| Ex. No. | Oxo-alcohols | temperature to which cooled and filtered (°C.) | branched-chain components in liquid phase (% by weight) | mean molecular weight of oxo-alcohols in liquid phase |
|---|---|---|---|---|
| 5 | OA-123 | −51.6 | 97.0 | 194.61 |
| 6 | OA-145 | −41.4 | 98.7 | 221.21 |

TABLE 3

Solvent: n-pentane
Volumetric ratio oxo-alcohols/solvent = 40:60

| Ex. No. | Oxo-alcohols | temperature to which cooled and filtered (°C.) | branched-chain components in liquid phase (% by weight) | mean molecular weight of oxo-alcohols in liquid phase |
|---|---|---|---|---|
| 7 | OA-125 | −50.9 | 95.8 | 207.0 |
| 8 | OA-123 | −49.9 | 95.5 | 193.71 |
| 9 | OA-145 | −41.3 | 98.7 | 221.2 |

TABLE 4

Solvent: n-pentane
Volumetric ratio oxo-alcohols/solvent = 50:50

| Ex. No. | Oxo-alcohols | temperature to which cooled and filtered (°C.) | branched-chain components in liquid phase (% by weight) | mean molecular weight of oxo-alcohols in liquid phase |
|---|---|---|---|---|
| 10 | OA-123 | −47.2 | 96.3 | 194.60 |
| 11 | OA-145 | −33.6 | 97.7 | 221.20 |

From the aforegoing data it can be seen that the treatment is selective towards linear oxo-alcohols, which are separated in the practically pure form, and that the treatment does not alter the mean molecular weight of the oxo-alcohols, so that the two separated fractions (linear and branched-chain) each have the same mean molecular weight as the initial mixture.

EXAMPLES 12 AND 13

The tests of these examples are conducted in an insulated, jacketed vessel having a volume of approximately 10 liters, fitted with an anchor agitator, a temperature measurement device and a bottom outlet. This latter is connected to a basket centrifuge having a diameter of 20 cm, the basket being of medium metal mesh, felt and 5μ polypropylene filter cloth.

5 liters of a solution of oxo-alcohols in the chosen solvent are fed into the vessel, and the vessel contents are agitated and cooled to the predetermined temperature. When the solid/liquid system has reached equilibrium, the bottom valve is opened and the vessel contents are continuously fed to the centrifuge, operating at 3000 r.p.m.

The solid is melted by allowing the temperature to rise to ambient temperature, and is then subjected to gas chromatography analysis. The liquid phase (filtrate) is also subjected to gas chromatography analysis after evaporating the solvent. The results of these determinations are shown in Table 5, together with the other test conditions.

TABLE 5

Solvent: n-pentane
Volumetric ratio oxo-alcohols/solvent = 40:60

| Example no. | 12 | 13 |
|---|---|---|
| Oxo-alcohols | OA-123 | OA-145 |
| Temperature to which cooled (°C.) | -51 | -50 |
| Centrifuging temperature (°C.) | -35 | -35 |
| Branched-chain components in liquid phase (% by weight) | 96.2 | 94.7 |
| Mean molecular weight oxo-alcohols in liquid phase | 194.71 | 220.30 |
| Linear-chain components in solid phase (% by weight) | 91.8 | 93.4 |
| Mean molecular weight oxo-alcohols in solid phase | 195.70 | 219.20 |

EXAMPLES 14–19

The tests of these examples are conducted in an insulated, jacketed vessel with a useful capacity of 300 liters, fitted with an agitator, a temperature measurement device and a bottom outlet. This latter is connected to a centrifuge-decanter.

300 liters of a solution of oxo-alcohols in the chosen solvent are fed into the vessel, and the vessel contents are agitated and cooled to the predetermined temperature.

When the solid/liquid system has reached equilibrium, the bottom valve is opened and the vessel contents are transferred by a gear pump to the centrifuge-decanter in order to separate the liquid phase from the solid phase.

The solid is melted by allowing its temperature to rise to ambient temperature, after which it is subjected to gas chromatography analysis.

The liquid phase is also subjected to analysis after evaporating the solvent. The results of these determinations are shown in Tables 6 and 7, together with the other test conditions.

TABLE 6

Solvent: n-pentane
Oxo-alcohols: OA-123
Volumetric ratio oxo-alcohols/solvent = 50:50

| Example No. | 14 | 15 | 16 |
|---|---|---|---|
| Temperature to which cooled (°C.) | −46 | −50 | −48 |

TABLE 6-continued

Solvent: n-pentane
Oxo-alcohols: OA-123
Volumetric ratio oxo-alcohols/solvent = 50:50

| Example No. | 14 | 15 | 16 |
|---|---|---|---|
| Gear pump throughput (1/hour) | 1130 | 1270 | 1310 |
| Centrifuging temperature (°C.) | −37 | −44 | −40 |
| Branched-chain components in liquid phase (% by weight) | 95.0 | 96.13 | 95.13 |
| Mean molecular weight oxo-alcohols in liquid phase | 194.4 | 194.5 | 194.1 |
| Linear-chain components in solid phase (% by weight) | 77.50 | 76.53 | 77.64 |
| Mean molecular weight oxo-alcohols in solid phase | 192.5 | 192.4 | 192.5 |

TABLE 7

Solvent: n-pentane
Oxo-alcohols: OA-145
Volumetric ratio oxo-alcohols/solvent = 50:50

| Example No. | 17 | 18 | 19 |
|---|---|---|---|
| Temperature to which cooled (°C.) | −45 | −40 | −50 |
| Gear pump throughput (1/hour) | 800 | 750 | 750 |
| Centrifuging temperature (°C.) | −37 | −30 | −34 |
| Branched-chain components in liquid phase (% by weight) | 95.90 | 98.20 | 97.70 |
| Mean molecular weight oxo-alcohols in liquid phase | 220.0 | 220.0 | 220.0 |
| Linear-chain components in solid phase (% by weight) | 78.30 | 73.05 | 71.50 |
| Mean molecular weight oxo-alcohols in solid phase | 218.8 | 219.1 | 219.1 |

We claim:

1. A process for preparing linear chain oxo-alcohols from a mixture containing linear and branched chain oxo-alcohols comprising:

dissolving a mixture of linear and branched chain detergent oxo-alcohols containing from 11 to 16 carbon atoms in the molecule in a liquid hydrocarbon solvent containing from 3 to 5 carbon atoms in the molecule, or in a methyl tert-butylether, in a volumetric constituent ratio of detergent oxo-alcohols to solvent which is in a range between 25:75 and 50:50;

cooling the resultant solution to a temperature in a range of −20° C. to −52° C. until a solid phase, dispersed in a liquid phase, separates;

separating and recovering said solid phase constituting the linear chain oxo-alcohol fraction from said liquid phase; and separating and recovering the branched chain oxo-alcohol fraction from said liquid phase.

2. A process according to claim 1 wherein the content of the linear chain detergent oxo-alcohol fraction in the linear and branched chain detergent oxo-alcohol mixture is between about 40% and 80% by weight.

3. A process according to claim 1 wherein the mixture of linear and branched chain detergent oxo-alcohols contains alcohols having from 12 to 15 carbon atoms in the molecule.

4. A process according to claim 1 wherein the liquid hydrocarbon solvent is selected from propane, n-butane, isobutane, n-pentane and isopentane.

5. A process according to claim 1 wherein the solid phase is separated from the liquid phase at a temperature between −20° C. and −52° C.

6. A process according to claim 1 wherein the solid phase is separated from the liquid phase at a temperature approximately equal to the precipitation temperature of the solid phase.

* * * * *